(12) United States Patent
Justice et al.

(10) Patent No.: US 10,214,781 B2
(45) Date of Patent: Feb. 26, 2019

(54) LPS SEROTYPES FOR DETERMINING SEVERITY OF URINARY TRACT INFECTION

(71) Applicant: RESEARCH INSTITUTE AT NATIONWIDE CHILDREN'S HOSPITAL, Columbus, OH (US)

(72) Inventors: Sheryl S. Justice, Westerville, OH (US); Kevin M. Mason, Blacklick, OH (US)

(73) Assignee: RESEARCH INSTITUTE AT NATIONWIDE CHILDREN'S HOSPITAL, Columbus, OH (US)

( * ) Notice: Subject to any disclaimer, the term of this patent is extended or adjusted under 35 U.S.C. 154(b) by 0 days.

(21) Appl. No.: 15/180,352

(22) Filed: Jun. 13, 2016

(65) Prior Publication Data

US 2016/0312270 A1    Oct. 27, 2016

Related U.S. Application Data

(63) Continuation-in-part of application No. PCT/US2014/070245, filed on Dec. 13, 2014.

(60) Provisional application No. 61/915,562, filed on Dec. 13, 2013.

(51) Int. Cl.
| | |
|---|---|
| *C12Q 1/689* | (2018.01) |
| *A61K 39/02* | (2006.01) |
| *G01N 33/569* | (2006.01) |
| *G01N 33/68* | (2006.01) |

(52) U.S. Cl.
CPC .............. *C12Q 1/689* (2013.01); *A61K 39/02* (2013.01); *G01N 33/56911* (2013.01); *G01N 33/6893* (2013.01); *G01N 2800/348* (2013.01)

(58) Field of Classification Search
None
See application file for complete search history.

(56) References Cited

FOREIGN PATENT DOCUMENTS

EP    0233048 B1    2/1992

OTHER PUBLICATIONS

Brooks et al. The Journal of Hygiene, vol. 87, No. 1 (Aug. 1981), pp. 53-61.*
Blanco et al. European Journal of Epidemiology 12:191-198, 1996.*
Kudinha et al. Clinical Microbiology and Infection, vol. 19, No. 4, p. E173-E180, Apr. 2013, published online Jan. 17, 2013.*
Billips, Benjamin K., Anthony J. Schaeffer, and David J. Klumpp. "Molecular basis of uropathogenic Escherichia coli evasion of the innate immune response in the bladder." Infection and immunity 76.9 (2008): 3891-3900.
Billips, Benjamin K., et al. "Modulation of host innate immune response in the bladder by uropathogenic Escherichia coli." Infection and immunity 75.11 (2007): 5353-5360.
Borchert, D., et al. "Prevention and treatment of urinary tract infection with probiotics: Review and research perspective." Indian Journal of Urology 24.2 (2008): 139.
Debroy, Chitrita, Elisabeth Roberts, and Pina M. Fratamico. "Detection of O antigens in Escherichia coli." Animal Health Research Reviews 12.02 (2011): 169-185.
Foxman, Betsy. "The epidemiology of urinary tract infection." Nature Reviews Urology 7.12 (2010): 653-660.
Horvath, Dennis J., et al. "Morphological plasticity promotes resistance to phagocyte killing of uropathogenic Escherichia coli." Microbes and Infection 13.5 (2011): 426-437.
Hunstad, David A., et al. "Suppression of bladder epithelial cytokine responses by uropathogenic Escherichia coli." Infection and immunity 73.7 (2005): 3999-4006.
Hunstad, David A., and Sheryl S. Justice. "Intracellular lifestyles and immune evasion strategies of uropathogenic Escherichia coli." Annual review of microbiology 64 (2010): 203-221.
Johnson, James R., and Adam L. Stell. "Extended virulence genotypes of Escherichia coli strains from patients with urosepsis in relation to phylogeny and host compromise." Journal of Infectious Diseases 181.1 (2000): 261-272.
Justice, Sheryl S., et al. "Differentiation and developmental pathways of uropathogenic Escherichia coli in urinary tract pathogenesis." Proceedings of the National Academy of Sciences of the United States of America 101.5 (2004): 1333-1338.
Justice, Sheryl S., et al. "Maturation of intracellular Escherichia coli communities requires SurA." Infection and immunity 74.8 (2006): 4793-4800.
Kim, Ji Hyun, et al. "Gram-negative and Gram-positive bacterial extracellular vesicles." Seminars in cell & developmental biology. vol. 40. Academic Press, 2015.
Lewicky, Jordan D., Marina Ulanova, and Zi-Hua Jiang. "Improving the immunostimulatory potency of diethanolamine-containing lipid A mimics." Bioorganic & medicinal chemistry 21.8 (2013): 2199-2209.
Li, Dan, et al. "A multiplex PCR method to detect 14 Escherichia coli serogroups associated with urinary tract infections." Journal of microbiological methods 82.1 (2010): 71-77.
Mohseni, Mohammad-Javad, et al. "Combination of probiotics and antibiotics in the prevention of recurrent urinary tract infection in children." Iranian journal of pediatrics 23.4 (2013): 430.
Mulvey, Matthew A., Joel D. Schilling, and Scott J. Hultgren. "Establishment of a persistent Escherichia coli reservoir during the acute phase of a bladder infection." Infection and immunity 69.7 (2001): 4572-4579.
Needham, Brittany D., et al. "Modulating the innate immune response by combinatorial engineering of endotoxin." Proceedings of the National Academy of Sciences 110.4 (2013): 1464-1469.

(Continued)

*Primary Examiner* — Oluwatosin A Ogunbiyi
(74) *Attorney, Agent, or Firm* — Tarolli, Sundheim, Covell & Tummino LLP

(57) ABSTRACT

A method of identifying a subject having a urinary tract infection posing a significant risk of dangerous sequalae is described. The method includes obtaining a urine or fecal sample from the subject; determining the predominant LPS O-antigen serotype in the sample; and comparing the predominant LPS O-antigen serotype to a set of febrile UTI LPS serotypes. The method can also include treating the subject for UTI if the predominant O-antigen LPS serotype is a febrile UTI LPS serotype.

12 Claims, 9 Drawing Sheets

(56) References Cited

OTHER PUBLICATIONS

Needham, Brittany D., and M. Stephen Trent. "Fortifying the barrier: the impact of lipid A remodelling on bacterial pathogenesis." Nature Reviews Microbiology 11.7 (2013): 467-481.

Orenstein, Robert, and Edward S. Wong. "Urinary tract infections in adults." American family physician 59.5 (1999): 1225-34.

Perry, Malcolm B., et al. "Identification of Escherichia coli serotype O157 strains by using a monoclonal antibody." Journal of clinical microbiology 26.11 (1988): 2391-2394.

Raetz, Christian RH, and Chris Whitfield. "Lipopolysaccharide endotoxins." Annual review of biochemistry 71 (2002): 635.

Schilling, Joel D., et al. "CD14- and Toll-like receptor-dependent activation of bladder epithelial cells by lipopolysaccharide and type 1 piliated Escherichia coli." Infection and immunity 71.3 (2003): 1470-1480.

Schilling, Joel D., et al. "Toll-like receptor 4 on stromal and hematopoietic cells mediates innate resistance to uropathogenic Escherichia coli." Proceedings of the National Academy of Sciences 100.7 (2003): 4203-4208.

Schwartz, Drew J., et al. "Uropathogenic Escherichia coli superinfection enhances the severity of mouse bladder infection." PLoS Pathog 11.1 (2015): e1004599.

Sharpe, Samantha W., Meta J. Kuehn, and Kevin M. Mason. "Elicitation of epithelial cell-derived immune effectors by outer membrane vesicles of nontypeable Haemophilus influenzae." Infection and immunity 79.11 (2011): 4361-4369.

Sheu, Ji-Nan, et al. "Relationship between serum and urine interleukin-6 elevations and renal scarring in children with acute pyelonephritis." Scandinavian journal of urology and nephrology 43.2 (2009): 133-137.

Stenutz, Roland, Andrej Weintraub, and Goran Widmalm. "The structures of Escherichia coli O-polysaccharide antigens." FEMS microbiology reviews 30.3 (2006): 382-403.

Storm, Douglas W., et al. "Relationship among bacterial virulence, bladder dysfunction, vesicoureteral reflux and patterns of urinary tract infection in children." The Journal of urology 188.1 (2012): 236-24.

Wullt, Björn, et al. "The role of P fimbriae for Escherichia coli establishment and mucosal inflammation in the human urinary tract." International journal of antimicrobial agents 19.6 (2002): 522-538.

Wurpel, Daniël J., et al. "Comparative analysis of the uropathogenic Escherichia coli surface proteome by tandem mass-spectrometry of artificially induced outer membrane vesicles." Journal of proteomics 115 (2015): 93-106.

PCT International Search Report and Written Opinion for PCT/US14/70245, dated Mar. 16, 2015, pp. 1-9.

* cited by examiner

LPS SEROTYPES FOR DETERMINING SEVERITY OF URINARY TRACT INFECTION

CROSS-REFERENCE TO RELATED APPLICATIONS

This application claims priority to International Patent Application No. PCT/US2014/070245, filed on Dec. 13, 2014, which claims priority to U.S. Provisional Application Ser. No. 61/915,562, filed on Dec. 13, 2013, both of which are hereby incorporated by reference in its entirety.

BACKGROUND

The pediatric kidney is sensitive to scarring as a consequence of urinary tract infections (UTIs). Prevention of renal scars is paramount, as the associated damage may lead to long-term health issues including chronic renal failure. UTIs afflict up to 17% of girls, account for 5% of febrile conditions treated in emergency departments and 2% of pediatric hospitalizations, culminating in over $8 billion in medical expenditures each year. UTI is one of the most common reasons for short duration antibiotic exposure for acute treatment and long-term prophylactic antibiotic therapies to prevent recurrent UTI during childhood. In addition to the rise in antibiotic resistant organisms causing UTI, there is accumulating evidence that antibiotic use during childhood increases the susceptibility for chronic health problems (e.g. asthma, obesity, gastrointestinal diseases). Therefore, UTIs represent a significant health concern, particularly for the pediatric population.

There are multiple factors that confound the diagnosis of UTI. Uropathogenic *Escherichia coli* (UPEC), the most common causative agent of UTIs, is a member of a bacterial species that includes strains that range from non-pathogenic commensals to hemorrhagic diarrheal strains. Foxman B., Nat Rev Urol. December; 7(12):653-660 (2010). Non-pathogenic strains of *E. coli* are normal constituents of the gastrointestinal microbiome that can easily contaminate urine samples during specimen collection. Current clinical diagnostics do not distinguish non-pathogenic from uropathogenic strains of *E. coli* making diagnosis problematic, particularly in pediatric patients where clean sample collection is difficult. The symptoms associated with UTI are often difficult for children to report and are non-specific. Clinical differentiation between cystitis and pyelonephritis requires a reliable historian, and has important implications for long-term consequences. Therefore, there is a critical need for novel point of service diagnostics to objectively diagnose UTI.

SUMMARY

Urinary tract infection (UTI) is one of the most common ailments requiring antibiotic therapies as well as prolonged prophylaxis to prevent recurrent infections. Management of UTI for children is problematic due to the difficulty in reporting symptoms, poor reliability with current point of service diagnostics and the days needed for culture proven diagnosis. Furthermore, the lack of predictive tools for potential risk of development for severe disease and renal scaring can lead to unnecessary antibiotic exposure. Therefore, there is a critical need for novel approaches to diagnose UTI to promote antibiotic stewardship. The inventors hypothesized that bacterial traits associated with modulation of proinflammatory responses elicited during UTI are convenient markers to identify uropathogenic strains of *E. coli* as well as predict the potential for severe disease.

Bacteria were isolated from the urine of children seeking treatment for non-febrile or febrile UTI and used in experimental models of infection to identify bacterial traits that are predictive for the severity of clinical disease. The magnitude of systemic proinflammatory responses during experimental UTI correlates with bacterial persistence and the severity of clinical UTI. The lipopolysaccharide (LPS) serotype correlates with the magnitude of proinflammatory responses and is predictive for the severity of clinical UTI. The data suggest that the LPS serotype is a convenient urinary marker to assist in management of patients indicated for treatment of UTI due to an association of the magnitude of cytokine elicitation with the risk for development of severe infection.

BRIEF DESCRIPTION OF THE FIGURES

The accompanying drawings, which are incorporated in and constitute a part of this specification, illustrate some embodiments disclosed herein, and together with the description, serve to explain principles of the disclosed embodiments.

DETAILED DESCRIPTION

Figure 1A:
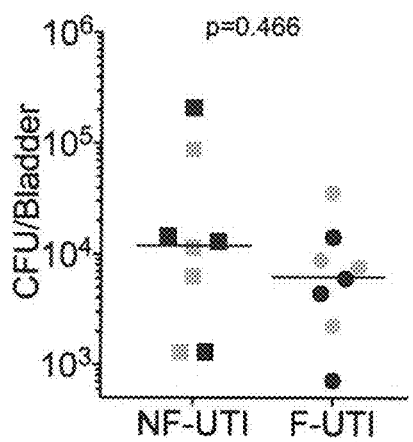
FIGS. 1A-1E provide graphs and images showing the colonization and microscopic examination of UPEC clinical isolates associated with febrile and non-febrile UTI. Female mice (n=4 per cohort) were inoculated with 107 colony forming units (CFU) of either a UPEC non-febrile isolate (NF-UTI; PEDS177 gray square; PEDS914 black square) or febrile isolate (F-UTI; PEDS175 gray circle; PEDS939 black circle). The serotype of each strain is indicated in the legend. Organs indicated were harvested at 6 hours post infection for homogenization and enumeration of bacteria as total CFU per organ. Statistical significance was determined using two-tailed Mann-Whitney U test. Additional bladders were bisected, splayed, fixed and stained for microscopic examination of intracellular bacterial communities (green) within the epithelial cells (blue nuclei). Representative intracellular communities of UTI89, PEDUTI177 and PEDUTI939 are presented (C-E). Scale bar=10 μm.
Figure 1B:
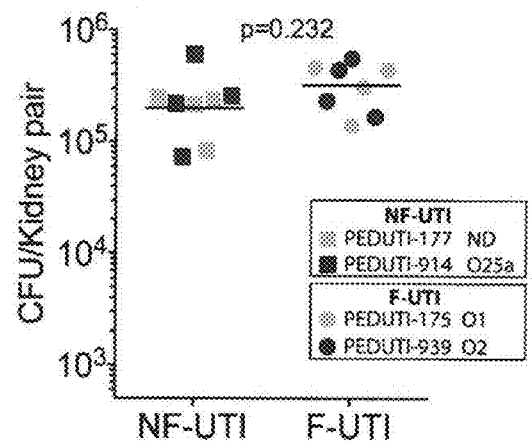

A method of identifying and treating a subject for a urinary tract infection (UTI) having a significant risk of dangerous sequalae is described. The method includes obtaining a urine or fecal sample from the subject; determining the predominant LPS O-antigen serotype in the sample; comparing the predominant LPS O-antigen serotype to a set of febrile UTI LPS serotypes; and treating the subject for UTI if the predominant O-antigen LPS serotype is a febrile UTI LPS serotype.

As used herein, the term "diagnosis" can encompass determining the likelihood that a subject will develop a disease, or the existence or nature of disease in a subject. The term diagnosis, as used herein also encompasses determining the severity and probable outcome of disease or episode of disease or prospect of recovery, which is generally referred to as prognosis).

As used herein, the terms "treatment," "treating," and the like, refer to obtaining a desired pharmacologic or physiologic effect. The effect may be therapeutic in terms of a partial or complete cure for a disease or an adverse effect attributable to the disease. "Treatment," as used herein, covers any treatment of a disease in a mammal, particularly in a human, and can include inhibiting the disease or condition, i.e., arresting its development; and relieving the disease, i.e., causing regression of the disease.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a sample" includes a plurality of such samples.

Unless otherwise indicated, all numbers expressing quantities of ingredients, properties such as molecular weight, reaction conditions, and so forth as used in the specification and claims are to be understood as being modified in all instances by the term "about." Accordingly, unless otherwise indicated, the numerical properties set forth in the following specification and claims are approximations that may vary depending on the desired properties sought to be obtained in embodiments of the present invention. Notwithstanding that the numerical ranges and parameters setting forth the broad scope of the invention are approximations, the numerical values set forth in the specific examples are reported as precisely as possible. Any numerical values; however, inherently contain certain errors necessarily resulting from error found in their respective measurements.

The terms "subject," and "patient" are used interchangeably herein, and generally refer to a mammal, including, but not limited to, primates, including simians and humans, equines (e.g., horses), canines (e.g., dogs), felines, various domesticated livestock (e.g., ungulates, such as swine, pigs, goats, sheep, and the like), as well as domesticated pets and animals maintained in zoos. Treatment and evaluation of humans is of particular interest.

Urinary Tract Infection

A urinary tract infection (UTI), as defined herein, is an infection of any part of the urinary tract. The urinary tract includes the kidneys, the bladder, the urethra, and the ureter. Infection of the urinary tract typically results in a variety of symptoms, depending on the specific site of infection. Infection of the kidneys (e.g., acute pyelonephritis) can result in upper back and side pain, high fever, shaking and chills, nausea, and vomiting. Infection of the bladder (e.g., cystitis) can result in pelvic pressure, lower abdomen discomfort, frequent and painful urination, and blood in the urine. Infection of the urethra (e.g., urethritis) typically can be diagnosed based on a burning sensation associated with urination. One or more of these conditions can indicate a urinary tract infection, though it is preferable to confirm the presence of infection since there are other conditions such as irritation of the urethra, vaginitis, interstitial cystitis, or sexually transmitted diseases that can replicate some of these symptoms. For febrile UTI, a fever will be present, and possibly other associated symptoms such as shaking and chills as well.

Urinary tract infections can be acute or chronic. An acute UTI is typically short term (i.e., less than one month) and of high intensity, whereas a chronic infection is a longer-term infection (i.e., lasting at least one month, and up to a number of years). In a chronic infection and/or colonization, the patient typically has bacteria growing in their bladder but they do not have symptoms typically associated with a urinary tract infection. An acute infection is present when the patient has symptoms such as painful urination or fever. A fever, as defined herein, is a body temperature above 100° F. If an acute infection is present simultaneously with a chronic infection, the effects of the acute infection will dominate those of the chronic infection in terms of overall characterization of the infection, for at least the reason that a chronic infection typically shows few effects.

In some embodiments, the subject is a subject who has an increased risk of having a urinary tract infection. An increased risk refers to a higher likelihood or percent possibility of having a urinary tract infection in comparison with a subject who is not at an increased risk. For example, urinary tract infections occur most frequently in boys and girls during the first year of life. The likelihood of a urinary tract infection drops sharply after the first year, but then gradually increases with age. Gender is also a factor, with women having a high rate of UTIs due to physiological differences. The risk of having a UTI increases even further after menopause in women, and in pregnant women. Andriole, V. T., Patterson, T. F., Med. Clin. North. Am. 75, 359-373 (1991). Other risk factors for a urinary tract infection include taking antibiotics, having a urinary catheter inserted or having surgery on the urinary tract, a high level of sexual activity (Scholes et al., J. Infect Dis. 182, 1177-1182 (2000)), and various diseases or disorders such as urinary tract anatomical defects, vesicoureteral reflux, diabetes, weakened immune system, kidney stones, an enlarged prostate, body paralysis, a history of kidney transplant, HIV status, sickle cell anemia, and nervous system disorders affecting bladder emptying.

Urinary tract infections can also be asymptomatic. Asymptomatic bacteriuria is a colonization of a portion of the urinary tract by bacteria that does not display the symptoms typically seen for a urinary tract infection. The urine samples obtained from a subject with asymptomatic bacteriuria may look infected (as evaluated by dipstick, for example) and will result in bacterial growth if cultured. However, it is difficult to determine if this represents an early infection that can be treated briefly to avoid complications, or just bladder colonization with non-pathogenic bacteria that does not represent a problem and will likely not be cleared by treatment with antibiotics. Not all asymptomatic infections represent chronic infections. Some types of subjects will be asymptomatic as a result of a lack of inflammatory response due to immunosuppression (e.g., transplant patients) or lack of sensation of symptoms as a result of, for example, having spinal cord injuries or congenital spinal/neural tube defects.

A urinary tract infection is typically a bacterial infection. The bacteria can be gram-negative bacteria, or the bacterial can be gram-positive bacteria. For example, the bacteria can be one or more of *E. coli, Pseudomonas, Enterococcus, Enterobacter, Klebsiella,* or *Proteus mirabilis.* The majority (80-85%) of bacterial urinary tract infections are caused by *E. coli.* However, a urinary tract infection can also occur as a result of infection by pathogens other than bacteria. For example, urinary tract infections can also be caused by viruses and fungus. Examples of urinary viral infections include those by BK virus, cytomegalovirus (CMV) and Epstein-Barr virus (EBV). Fungal infection is commonly caused by infection by fungi of the genus *Candida.*

Urinary tract infection can also lead to further problems. As described herein, identification of certain predominant LPS O-antigen serotypes in a sample obtained from a subject can indicate that the subject has an increased or significant risk of developing dangerous sequalae. Secondary pathological conditions resulting from a urinary tract infection, also known as complications or dangerous sequala, include renal scarring, urosepsis, adverse perinatal outcomes, and pyelonephritis. Dangerous sequalae are significantly more likely to occur when a subject is infected by more severe UTI, such as a UTI involving the development of a fever.

Treatment of Urinary Tract Infection

A variety of methods are known for treating a urinary tract infection. Typically, this is done with a therapeutic agent. For example, in some embodiments, the therapeutic agent is an antibiotic. Examples of suitable antibiotics include trimethoprim-sulfamethoxazole, cephalosporins, nitrofurantoin, amoxicillin, Augmentin™, doxycycline, and fluoroquinolones. Pyelonephritis is treated more aggressively than a simple bladder infection using either a longer course of oral antibiotics or intravenous antibiotics. For a description of the various treatment methods for various types of urinary tract infection, see Orenstein et al., Am. Fam. Physician., 59(5): 1225-1234 (1999), the disclosure of which is incorporated by reference herein.

Urinary tract infections can also be treated with analgesics to relieve the burning pain and urgent need to urinate. For example, the local analgesic phenazopyridine hydrochloride (Pyridium®) can be used together with an antibiotic for treatment of a urinary tract infection.

In some embodiments, a urinary tract infection can be treated by administration of a probiotic to the subject. Probiotics are defined as live microorganisms which when administered in adequate amounts confer a health benefit to the subject. Preferred probiotics for the present invention are non-pathogenic, and/or non-fever-inducing bacteria, such as *Lactobacillus* bacteria. The presence of benign bacterial flora is important for body function and prevention of infection by pathogenic bacteria. Probiotics can be administered orally, or can be administered directly to the urinary tract. Methods of treating urinary tract infection by administration of probiotics are known to those skilled in the art. Borchert et al., Indian J. Urol. 24, 139-144 (2008).

Lipopolysaccharide Serotypes

Lipopolysaccharides (LPS), also known as lipoglycans, are large molecules consisting of a lipid and a polysaccharide joined by a covalent bond that are typically found in the outer membrane of Gram-negative bacteria. Lipopolysaccharides consist of three parts: the O-antigen, the core oligosaccharide, and Lipid A. The serotyping of *E. coli* is based on the somatic (O), flagellar (H) and capsular polysaccharide antigens (K). *E. coli* serotypes are of particular interest as *E. coli* is a common cause for UTI. Accordingly, in some embodiments, the predominant O-antigen LPS serotype is an *E. coli* LPS serotype. However, all other gram-negative bacteria also can be serotyped using antigens such as O-antigens. The O-antigen is a repetitive glycan polymer that comprises the outermost domain of an LPS molecule. The composition of the O-antigen varies from strain to strain, and there are over 160 different O-antigens produced by different *E. coli* strains. Raetz, C. and Whitfield, C., Annu. Rev. Biochem. 71, 635-700 (2002). The O-antigens for *E. coli* are described by an *E. coli* O-antigen database. Stenutz, R., and Weintraub, A., FEMS Microbiol. Rev. 30, 382-403 (2006), the disclosure of which is incorporated herein by reference.

Methods of identifying a subject having a urinary tract infection that poses a significant risk of dangerous sequalae can involve detecting a variety of different LPS-O-antigen serotypes associated with urinary tract infections. One aspect of the invention provides a method of identifying and treating a subject for a UTI having a significant risk of dangerous sequalae by obtaining a sample from the subject; determining the predominant LPS O-antigen serotype in the sample; and comparing the predominant LPS O-antigen serotype to a set of febrile UTI LPS serotypes. A UTI having a significant risk of dangerous sequalae can be a more severe form of UTI. Examples of febrile UTI LPS serotypes include, for example, serotypes O2, O16, and O25b. In some embodiments, the method will detect one or more serotypes known to be associated with pathogenic bacteria. Examples of serotypes associated with pathogenic bacteria include serotypes selected from the group consisting of O2, O16, O21, O25a, O25b, and O75. In some embodiments, the O-antigens in a sample are evaluated for their effect on cytokine production. For example, the method may detect an LPS-O-antigen serotype that elicits a low IL-6 response.

The methods generally involve detecting a plurality of LPS O-antigen serotypes, which are then compared to see which of the LPS O-antigen serotypes is the predominant serotype. A predominant serotype is the serotype that is present in a greater amount than any other serotype. In some embodiments, the serotype is predominant to a specified degree. For example, the predominant serotype may be present in a 10%, 20%, 30%, 40%, 50%, or a 100% greater amount than the serotype having the next highest amount. In situations where a plurality of O-antigen LPS serotypes all have the same highest level, they are all considered to be the predominant O-antigen. Alternately, rather than determining a predominant O-antigen, O-antigen levels can be compared to controls to determining whether a particular O-antigen is being expressed at higher than expected levels. Furthermore, in other embodiments, the level of the predominant O-antigen, or its level compared to a control, can be used a further indicator of disease severity.

Measuring Lipopolysaccharide Levels

In order to determine the predominant LPS serotype, a sample including LPS should be obtained. As the of the invention is directed towards identifying and treating a subject for a UTI having a significant risk of dangerous sequalae, the sample should be one including LPS associated with UTI. Examples of suitable samples include fecal samples and urine samples, with a urine sample being preferred. A variety of methods are known to those skilled in the art for obtaining a urine or fecal sample. Urine collected in a normal individual by suprapubic aspiration of the bladder is sterile and does not contain leukocytes. This method represents the ideal method for obtaining a urine sample. However, it is not performed routinely in clinical practice in which urine samples are generally obtained after natural micturition; in this setting, some degree of artifactual contamination with normal urethral organisms occurs.

A standard method for obtaining a urine sample can be referred to as the clean-catch sample method. To obtain an untainted urine sample, doctors usually request a so-called midstream, or clean-catch, urine sample. To provide this, the subject washes the area from which urine will issue, urinate a small amount into the toilet for a few seconds and then stop, position the container to catch the middle portion of the stream, urinate until the collection cup is halfway full (about 2 ounces), and then remove the cup. The collection cup should then be sealed with a cap and given to the doctor or sent to the laboratory for analysis.

Alternately, urine can be collection with a catheter. Some patients (small children, elderly people, or hospitalized patients) cannot provide a urine sample. In such cases, a catheter may be inserted into the bladder to collect urine. This is the best method for providing a contaminant-free sample, but has the disadvantage of possibly introducing or spreading infection.

The urine sample may be pretreated as necessary by dilution in an appropriate buffer solution and concentrated or fractionated by any number of methods including but not limited to ultracentrifugation, fractionation by fast performance liquid chromatography (FPLC), or precipitation. Any of a number of standard aqueous buffer solutions at physiological pH, such as phosphate, Tris, or the like, can be used.

Once a sample has been obtained, an analytic device is used to measure the levels of LPS. The analytic device can be either a portable or a stationary device. In addition to including equipment used for detecting the LPS, the analytic device can also include additional equipment to provide physical separation of analytes prior to analysis. For example, if the analyte detector is an immunoassay, it may also include an ion exchanger column chromatography to purify the proteins from urine before the specific detection of LPS O-antigens by immunoassay. Methods for detecting O-antigens are known to those skilled in the art. See DebRoy et al., Anim. Health Res. Rev. 12, 169-185 (2011), the disclosure of which is incorporated herein by reference. An alternate method for determining the predominant O-antigen LPS serotype is by using a polymerase chain reaction (PCR)-based assay, such as multiplex PCR.

Once the levels of LPS O-antigens have been determined, they can be displayed in a variety of ways. For example, the levels of LPS O-antigens can be displayed graphically on a display as numeric values or proportional bars (i.e., a bar graph) or any other display method known to those skilled in the art. The graphic display can provide a visual representation of the amounts of the various LPS O-antigens in the samples being evaluated. In addition, in some embodiments, the analytic device can also be configured to display a comparison of the levels of LPS O-antigens in the subject's urine to a control value based on levels of LPS O-antigens in a comparable urine sample, urine samples from a reference cohort, or a standard numerical reference.

Kits

Another aspect of the invention relates to kits for identifying a subject having a urinary tract infection posing a significant risk of dangerous sequalae. The kits include one or more probes capable of determining the amount of an LPS-O-antigen serotype in a urine or fecal sample. A kit generally includes a package with one or more containers holding the reagents, as one or more separate compositions or, optionally, as an admixture where the compatibility of the reagents will allow. The kits may further include enzymes (e.g., polymerases), buffers, labeling agents, nucleotides, controls, and any other materials necessary for carrying out purification and/or modification of the sample. In some embodiments, such kits may also include control reagents, e.g., known amounts of LPS O-antigen. Kits can also include a tool for obtaining a sample from a subject, such as a urine or feces receptacle or syringe.

The probes used in the kit can be selected to detect a variety of different LPS-O-antigen serotypes associated with urinary tract infections. In some embodiments, the probes will detect a serotype known to be associated with pathogenic bacteria. Examples of serotypes associated with pathogenic bacteria include serotypes selected from the group consisting of O2, O16, O21, O25a, O25b, and O75. In other embodiments, the probes will detect an LPS-O-antigen serotype that elicits a low IL-6 response. In other embodiments, the probes are suitable for determining the amount of an LPS-O-antigen serotype selected from the group consisting of serotypes O2, O16, and O25b.

In some embodiments, the probe is an antibody capable of specifically binding to LPS-O-antigens. Examples of antibodies that can be used in the present disclosure include, but are not limited to, polyclonal antibodies, monoclonal antibodies, chimeric antibodies, human antibodies, humanized antibodies, recombinant antibodies, single-chain Fvs ("scFv"), an affinity maturated antibody, single chain antibodies, single domain antibodies, F(ab) fragments, F(ab') fragments, disulfide-linked Fvs ("sdFv"), and antiidiotypic ("anti-Id") antibodies and functionally active epitope-binding fragments of any of the above.

As used herein, the term "specifically binding" refers to the interaction of the antibody with a second chemical species, wherein the interaction is dependent upon the presence of a particular structure (e.g., an antigenic determinant or epitope) on the chemical species; for example, an antibody recognizes and binds to a specific protein structure rather than to proteins generally.

The kits may also include a solid phase, to which the antibodies functioning as capture antibodies and/or detection antibodies in a sandwich immunoassay format are bound. The solid phase may be a material such as a magnetic particle, a bead, a test tube, a microtiter plate, a cuvette, a membrane, a scaffolding molecule, a quartz crystal, a film, a filter paper, a disc or a chip. The kit may also include a detectable label that can be or is conjugated to an antibody, such as an antibody functioning as a detection antibody. The detectable label can for example be a direct label, which may be an enzyme, oligonucleotide, nanoparticle chemiluminophore, fluorophore, fluorescence quencher, chemiluminescence quencher, or biotin. Test kits may optionally include any additional reagents needed for detecting the label.

In some embodiments, the probes are polynucleotides complementary to a portion of a gene expressing an LPS-O-antigen. A polynucleotide probe refers to a polynucleotide sequence capable of binding to a target nucleic acid of complementary sequence through one or more types of chemical bonds, usually through complementary base pairing, usually through hydrogen bond formation. Probes may bind target sequences lacking complete complementarity with the probe sequence, depending upon the stringency of the hybridization conditions. There may be any number of base pair mismatches which will interfere with hybridization between the target sequence and the single-stranded nucleic acids described herein. However, if the number of mutations is so great that no hybridization can occur under even the least stringent of hybridization conditions, the sequence is not a complementary target sequence. A probe may be single-stranded or partially single- and partially double-stranded. The strandedness of the probe is dictated by the structure, composition, and properties of the target sequence. Probes may be directly labeled or indirectly labeled such as with biotin to which a streptavidin complex may later bind.

In some embodiments, the kits can be designed for use with PCR methods, and further comprise reagents for use in the reverse transcription and amplification reactions. In some embodiments, the kits comprise enzymes such as reverse transcriptase, and a heat stable DNA polymerase, such as Taq polymerase. In some embodiments, the kits further comprise deoxyribonucleotide triphosphates (dNTP) for use in reverse transcription and amplification. In further embodiments, the kits comprise buffers optimized for specific hybridization of the probes.

The kit can also include instructions for using the kit to carry out a method of identifying a subject having a urinary tract infection posing a significant risk of dangerous sequalae. Examples of such information include, but are not limited to cut-off values, sensitivities at particular cut-off values, as well as other printed material for characterizing risk based upon the outcome of the assay. Instructions included in kits can be affixed to packaging material or can be included as a package insert. While the instructions are typically written or printed materials they are not limited to such. Any medium capable of storing such instructions and communicating them to an end user is contemplated by this disclosure. Such media include, but are not limited to, electronic storage media (e.g., magnetic discs, tapes, cartridges, chips), optical media (e.g., CD ROM), and the like. As used herein, the term "instructions" can include the address of an internet site that provides the instructions.

The present invention is illustrated by the following example. It is to be understood that the particular examples, materials, amounts, and procedures are to be interpreted broadly in accordance with the scope and spirit of the invention as set forth herein.

EXAMPLE

Association of O-Antigen Serotype with the Magnitude of Initial Systemic Cytokine Responses and Persistence in the Urinary Tract Interleukin-6 (IL-6) is present in human urine during acute UTI. Sheu J. N., et al., Scand. J. Urol. Nephrol. 43, 133-137 (2009). Prior studies indicate that independent UPEC isolates elicit varying degrees of IL-6 produced by cultured human bladder epithelial cells in vitro. Storm D. W., et al., J. Urol. 188, 236-241 (2012). Moreover, the inventors have observed an inverse association between the amount of IL-6 induction in vitro and clinical severity of UTI, suggesting that this phenotype may discriminate between isolates that cause cystitis and pyelonephritis. Storm D. W., et al., J. Urol. 188, 236-241 (2012). These observations were extended, and for the first time, a correlation between the magnitude of IL-6 elicited from cultured human bladder epithelial cells in vitro with the magnitude of systemic IL-6 in during experimental UTI in the murine model was demonstrated. The inventors further determined that the initial extent of systemic proinflammatory responses was associated with enhanced persistence of UPEC in the kidney during experimental UTI. In addition, the extent of IL-6 elicitation was associated with the LPS O-antigen serotype of the strain. Taken together, the experimental evidence provides insight into the molecular mechanisms that demarcate an infection that will be cleared in the bladder from an infection that will progress to a more severe and persistent disease in the kidney.

Methods

Collection of *E. coli* strains isolated from non-febrile and febrile UTIs. UPEC isolates were obtained from the urine of patients presenting to the urology service at Nationwide Children's Hospital's with UTIs. The ChildLab clinical microbiology laboratory at Nationwide Children's Hospital identified the bacterial species and determined a bacterial burden of at least 105 colony forming unit/milliliter (cfu/ml) of urine for each isolate. Storm D. W., et al., J. Urol. 188, 236-241 (2012). Patient gender, age and urinary tract diagnosis/etiology are indicated in Table 1. Patients were placed into one of four diagnostic and etiologic categories: 1) Neurogenic Bladder Group (NGB); 2) Vesicoureteral Reflux Group (VUR); 3) Bladder and Bowel Dysfunction (BBD) and 4) No Underlying UTI Etiology Group as previously described. Storm D. W., et al., J. Urol. 188, 236-241 (2012). Isolates were categorized as causing febrile UTI (clinical pyelonephritis) when patients presented with flank pain, leukocytosis, body temperature >38.5° C., and nausea and/or vomiting. Storm D. W., et al., J. Urol. 188, 236-241 (2012). This study was performed with the approval of the Institutional Review Board for human studies (OHRP Assurance No. FWA00002860) at the Research Institute at Nationwide Children's Hospital (IRB 12-00269). UTI89 is a prototypic non-febrile UPEC isolate obtained from a woman with cystitis. Mulvey M. A., et al., 2001. Infect. Immun. 69, 4572-4579 (2001).

TABLE 1

Patient and isolate characteristics

| Isolate no. | Patient gender[a] | Patient age (mo) | Diagnosis | UTI presentation | LPS serotype[b] |
|---|---|---|---|---|---|
| PEDUTI173 | M | 10 | NGB | Febrile | O8 |
| PEDUTI175 | M | 11 | VUR | Febrile | O1 |
| PEDUTI177 | F | 96 | BBD | Nonfebrile | ND |
| PEDUTI180 | M | 348 | NUE | Febrile | O4 |
| PEDUTI181 | F | 3 | VUR | Febrile | O6 |
| PEDUTI908 | F | 72 | BBD | Nonfebrile | O21 |
| PEDUTI910 | F | 96 | NUE | Nonfebrile | O7 |
| PEDUTI912 | F | 96 | BBD | Nonfebrile | O25a |
| PEDUTI914 | M | 132 | NBG | Nonfebrile | O25a |
| PEDUTI918 | F | 120 | BBD | Nonfebrile | O16 |
| PEDUTI919 | F | 36 | NGB | Nonfebrile | O2 |
| PEDUTI921 | F | 108 | BBD | Nonfebrile | ND |
| PEDUTI923 | F | 84 | BBD | Febrile | O2 |
| PEDUTI924 | F | 1 | NUE | Febrile | O21 |
| PEDUTI925 | F | 48 | NUE | Nonfebrile | O1 |
| PEDUTI928 | F | 108 | NGB | Nonfebrile | O21 |
| PEDUTI929 | F | 120 | BBD | Nonfebrile | ND |
| PEDUTI932 | F | 60 | VUR | Nonfebrile | O21 |
| PEDUTI933 | F | 96 | NUE | Febrile | O25b |
| PEDUTI934 | F | 48 | VUR | Febrile | O16 |
| PEDUTI935 | F | 132 | BBD | Nonfebrile | O75 |
| PEDUTI939 | F | 1 | NUE | Febrile | O2 |
| PEDUTI944 | F | 72 | NGB | Nonfebrile | O18 |
| PEDUTI950 | F | 204 | NUE | Febrile | O18 |
| PEDUTI953 | M | 24 | VUR | Febrile | ND |
| PEDUTI954 | F | 72 | BBD | Nonfebrile | O25a |
| PEDUTI958 | F | 252 | NGB | Nonfebrile | O18 |
| PEDUTI962 | F | 72 | BBD | Nonfebrile | O18 |
| PEDUTI964 | M | 11 | VUR | Febrile | O16 |
| PEDUTI966 | F | 1 | VUR | Febrile | O18 |
| PEDUTI967 | F | 72 | VUR | Febrile | O18 |
| PEDUTI968 | F | 96 | NUE | Nonfebrile | O75 |
| PEDUTI969 | F | 12 | NUE | Febrile | O18 |
| PEDUTI972 | M | 3 | NUE | Febrile | O2 |
| PEDUTI974 | F | 84 | NUE | Febrile | O25b |
| PEDUTI975 | M | 1 | VUR | Febrile | O2 |
| PEDUTI976 | F | 60 | BBD | Nonfebrile | O18 |
| PEDUTI982 | F | 2 | VUR | Febrile | O18 |
| PEDUTI984 | M | 3 | VUR | Febrile | O16 |
| PEDUTI985 | F | 1 | VUR | Febrile | O25b |
| PEDUTI987 | F | 1 | NUE | Febrile | O2 |
| PEDUTI988 | F | 71 | BBD | Nonfebrile | ND |

[a]F, female; M, male.
[b]ND, not determined.

Murine model of human UTI. Based upon the magnitude of cytokine elicitation induced by these strains in vitro as part of previous studies (Storm D. W., et al., J. Urol. 188, 236-241 (2012)) and empirical determination that these isolates exhibit similar infection kinetics in vivo as part of this study, PEDUTI177 and PEDUTI914 *E. coli* isolates were selected as representatives of the non-febrile (NF-UTI) isolates. PEDUTI175 and PEDUTI939 *E. coli* isolates were selected as representatives of the febrile (F-UTI) isolates. In addition, the isolates represent each of the four diagnostic and etiologic categories (Table 1). UTI89 and these four pediatric isolates were statically grown in LB broth (Fisher Scientific, Pittsburgh, Pa.) to saturation at 37° C. The presence of type 1 pili was confirmed by mannose-sensitive agglutination using *Saccharomyces cerevisiae*. Li B., et al., 2010 Microbes Infect. 12, 662-668 (2010). Seven- to nine-week-old female C3H/Hen mice (Harlan Laboratories, Indianapolis, Ind.) were anesthetized with 3% isoflurane and inoculated transurethrally with 50 µl containing 1×107 viable bacteria as described. Hung C. S., et al., Nat. Protoc. 4, 1230-1243 (2009). At the indicated time points post inoculation, the mice were humanely sacrificed for aseptic retrieval of bladder and kidney pairs for tissue homogenization and bacterial enumeration. Serum was collected at the time of tissue harvest and the magnitude of proinflammatory cytokines was determined using a Mouse Inflammation Cytokines Bead Array (BD Biosciences, San Jose, Calif.). Bolton M., et al., PLoS One 7, e33897 (2012). The serum cytokines were determined using two dilutions of the serum. The cytokines were evaluated on three independent occasions. All animal experiments were performed using accredited conditions for animal welfare approved by the Institutional Animal Care and Use Committee (Welfare Assurance Number A3544-01) at The Research Institute at Nationwide Children's Hospital (AR06-00119).

Microscopic evaluation of intracellular communities. Infected murine bladders were harvested at 6 hours post inoculation, bisected, splayed and fixed in 4% paraformaldehyde (EM Sciences, Hatfield, Pa.) in phosphate buffered saline (PBS; Sigma, St. Louis, Mo.) as described Hung C. S., et al., Nat. Protoc. 4, 1230-1243 (2009). For visualization of pediatric E. coli isolates, bladders were treated with 0.1% triton X-100 (Fisher Scientific, Pittsburgh, Pa.) in PBS to permeabilize the epithelial plasma membranes. Pediatric UPEC strains were visualized with the addition of rabbit anti-E. coli polyclonal antisera (US Biological, Salem, Mass.) diluted 1:200 in PBS/0.1% Triton X-100 at 23° C. for 1 hour. Bladders were washed with PBS for 3 times before the addition of Goat anti-Rabbit secondary IgG conjugated to Alexa-594 (Life Technologies, Carlsbad, Calif.) diluted 1:200 in PBS/0.1% Triton X-100 at 23° C. for 1 hour. Residual antibodies were removed by washing with PBS for 3 times. Bladders infected with UTI89/pANT4 (Justice S. S., et al., Proc. Nat. Acad. Sci. 101, 1333-1338 (2004)) required no specific staining for visualization of bacteria as this strain constitutively produces the green fluorescent protein. Bacterial and host DNA was visualized by the addition of Hoechst 34580 (Invitrogen, Carlsbad, Calif.) for 10 minutes. Bladders were mounted with ProLong Gold antifade reagent (Invitrogen). Images were acquired using an Axiovert 200 M inverted epifluorescence microscope equipped with a motorized stage, an Axiocam MRM CCD camera and the Apotome component to improve fluorescence resolution (Carl Zeiss, INC, Thornwood, N.Y.). The intensity of the fluorescent images was uniformly adjusted to all pixels within the image using the levels function in Adobe Photoshop (Adobe Systems Incorporated; San Jose, Calif.).

Preparation of conditioned medium from UPEC isolates. All UPEC isolates (20 NF-UTI, 22 F-UTI, UTI89) were grown to saturation in RPMI 1640 (HyClone Laboratories, Logan, Utah) supplemented with 10% heat-inactivated fetal bovine serum (Sigma, St. Louis, Mo.) at 37° C. overnight without shaking. Bacteria were removed from the saturated cultures by centrifugation and the supernatants were further clarified by passage through a 0.22 µm filter (EMD Millipore, Billerica, Mass.) to generate "conditioned medium."

To determine the contribution of shed LPS to the magnitude of cytokine elicitation, the conditioned medium obtained from UTI89 and the UPEC isolates was depleted of LPS by two sequential passages over a Detoxi-gel Endotoxin Column (Thermo Scientific, Rockford, Ill.) according to manufacturer's recommendation. The absence of viable bacteria in the clarified conditioned medium was verified by plating on LB agar (Fisher Scientific).

The contribution of outer membrane vesicles to the magnitude of cytokine elicitation was determined by further clarification of the conditioned medium to remove the outer membrane vesicles by ultracentrifugation at 38,000×g for 1 hour as previously described. Sharpe S. W., et al., Infect. Immun. 79, 4361-4369 (2011).

Elicitation of interleukin 6 (IL-6) from cultured human bladder epithelial cells in vitro. Use of conditioned medium to elicit cytokine production: T24 bladder epithelial cells (derived from human bladder carcinoma; ATCC HTB-4; Manassas, Va.) were grown in 24 well plates containing RPMI 1640 medium supplemented with 10% heat-inactivated fetal bovine serum at 37° C. in humidified atmosphere with 5% carbon dioxide. Confluent epithelial cell monolayers were washed with warm media and then overlaid with 500 µl of clarified conditioned medium and returned to the incubator for 2 hours. Culture supernatants were removed, clarified at 20,000×g for 5 minutes and frozen at −80° C.

Use of live bacteria to elicit cytokine production: T24 human bladder epithelial cell monolayers were grown in 24 well plates as described above. After washing with warm media, cells were infected with viable UPEC, grown in RPMI as described above, at a multiplicity of infection 10 bacteria per epithelial cell and returned to the incubator for 2 hours. Culture supernatants were removed, clarified at 20,000×g for 5 minutes and frozen at −80° C.

The magnitude of IL-6 accumulation within the epithelial cell culture supernatant was determined by enzyme-linked immunoabsorbant assay (eBioscience, San Diego, Calif.) as previously described. Storm D. W., et al., J. Urol. 188, 236-241 (2012). The triplicate values were averaged and plotted as individual points for each isolate tested. Due to daily variation in results, representative studies are depicted. Where indicated, purified E. coli LPS 0111:B4 (Sigma-Aldrich, Saint Louis, Mo.) was added to a final concentration of 1.25 µg/ml.

LPS serotype of strains was determined by PCR. Identification of the O-antigen LPS serotypes was determined by PCR (Table 1) using previously defined primers (39, 40) with genomic DNA purified from each isolate (Qiagen, Carlsbad, Calif.).

Statistical analysis. The significance of the results was determined using a two-tailed Mann-Whitney U-test, chi-square, or one-way ANOVA as indicated (GraphPad Software, La Jolla, Calif.).

Results

Figure 1C:
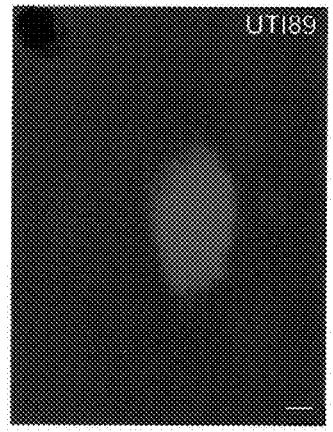
Figure 1D:
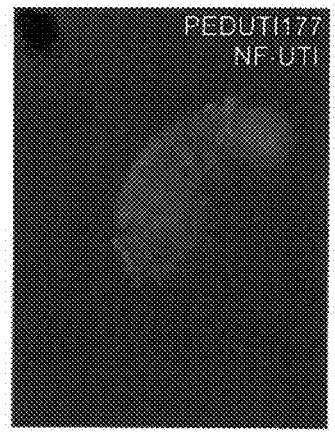
Figure 1E:
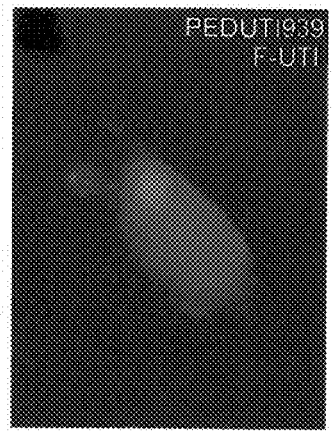

Magnitude of serum cytokines is associated with persistence during experimental UTI. Genetic differences between independent UPEC isolates as well as the multiplicity of infection can influence the kinetics of infection. Hunstad D. A. and Justice S. S., Annu. Rev. Microbiol. 64, 203-221 (2010); Billips B. K., et al., Infect. Immun. 76, 3891-3900 (2008). Therefore, the inventors sought to identify independent UPEC isolates from our library that exhibit similar infection kinetics during the first few hours of infection. These isolates would provide a means to determine the concordance of the cytokine profiles observed in vitro with those produced in response to experimental UTI. To this end, the kinetics of the initial stages of infection was first evaluated in the well-established mouse model of human UTI (Hung C. S., et al., Nat. Protoc. 4, 1230-1243 (2009)) using four pediatric UPEC isolates. Two representatives for each of the non-febrile and febrile isolates were chosen to increase the reliability of the results. There was no significant difference in the bacterial burden of either the urinary bladder or the kidney pairs 6 hours after introduction of any of the four representative UPEC isolates into the bladder (6 hours; FIG. 1A, B). Furthermore, the development of intracellular bacterial communities within superficial bladder epithelial cells were similar amongst these four representative UPEC isolates and as compared with the prototypical cystitis isolate, UTI89 (FIG. 1C, D, E). Justice S. S., et al., Proc. Nat. Acad. Sci. 101, 1333-1338 (2004). Therefore, as evidenced by the similarity in intracellular community development and bacterial burden, these isolates are appropriate for comparison of the immunomodulation capacity of each strain on initial proinflammatory responses during infection in vivo.

Figure 2:
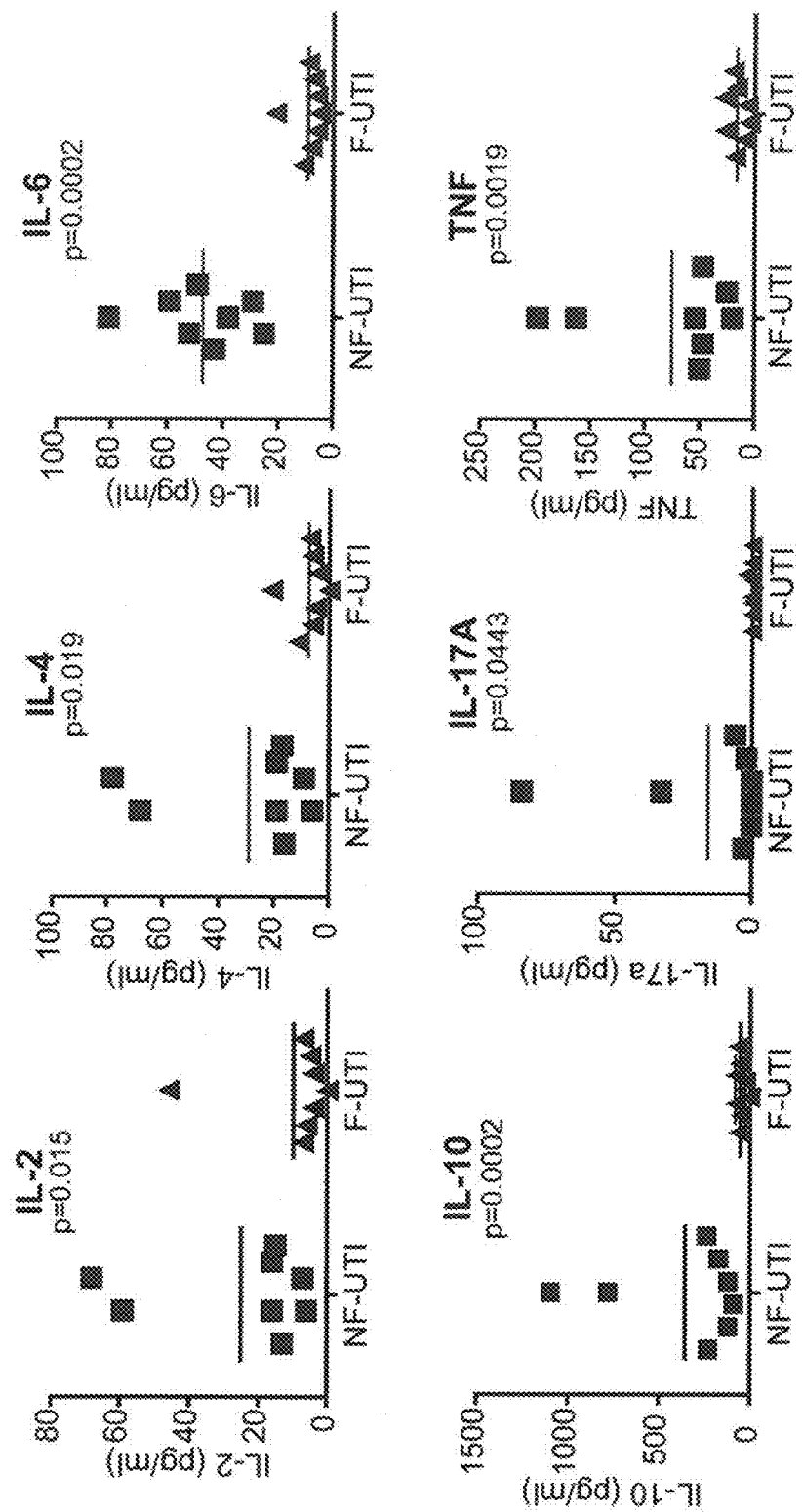
FIG. 2 demonstrates that non-febrile UTI isolates elicit higher magnitude of systemic cytokines. The magnitude of serum cytokines (pg/ml) 6 hours after intraurethral introduction of UPEC clinical isolates associated with febrile and non-febrile UTI. The serum obtained from each individual mouse was measured independently on two separate occasions. The averages were plotted. Statistical significance was determined using two-tailed Mann-Whitney U test.

The magnitude of systemic proinflammatory responses induced by each of the independent UPEC isolates during experimental UTI was evaluated. Consistent with the in vitro observations (Storm D. W., et al., J. Urol. 188, 236-241 (2012)), mice infected with the two representative non-febrile UPEC isolates (high elicitation of IL-6 in vitro) displayed a statistically significant increase in the magnitude of systemic IL-6 as compared with mice infected with the two representative febrile UPEC isolates (low elicitation of IL-6 in vitro) (FIG. 2). Although not as pronounced as in the case of IL-6, a statistically significant increase in IL-2, IL-4, IL-10, IL-17A and tumor necrosis factor (TNF) was also observed in the serum of mice infected with the two representative non-febrile UPEC isolates as compared with the two representative febrile UPEC isolates (FIG. 2). Therefore, the immunomodulation of cytokine production observed in vitro is recapitulated during infection in the host.

Figures 3A, 3B, 3C:
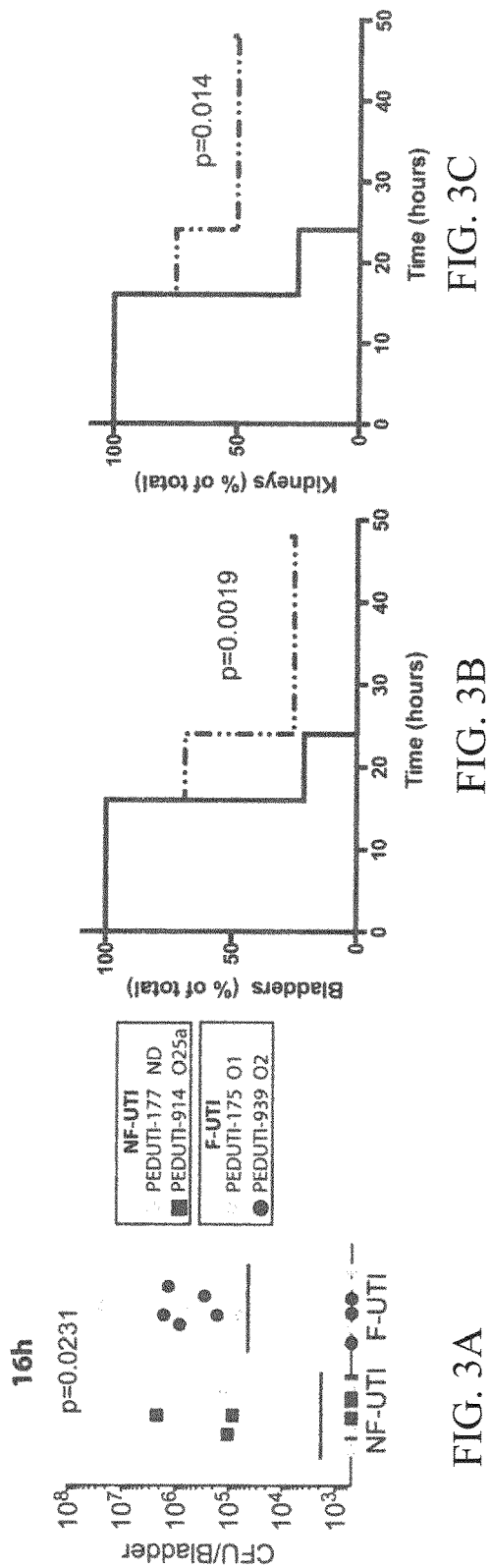
FIGS. 3A-3C provide graphs showing the persistence of UPEC clinical isolates associated with febrile and non-febrile UTI. Female mice (n=8 per cohort) were inoculated with 107 CFU of either a UPEC non-febrile isolate (NF-UTI; PEDS177 gray square; PEDS918 black square) or febrile isolate (F-UTI; PEDS175 gray circle; PEDS939 black circle). The serotype of each strain is indicated in the legend. Organs indicated were harvested at 16 hours post infection for homogenization and enumeration of bacteria. Statistical significance was determined using two-tailed Mann-Whitney U test. Bacterial persistence in the bladders (B) and the kidneys (C) of mice infected with non-febrile (solid line; n=9 mice each for PEDS177 and PEDS914 per time point) and febrile (dotted line; n=8 mice each for PEDS175 and PEDS175 per time point) UPEC isolates is presented as a percentage for 48 hours after inoculation. Statistical significance was determined by Chi square analysis.

To evaluate the consequences of modulation of proinflammatory responses on the manifestation of disease, the persistence of each of the four representative UPEC isolates was followed throughout the course of an acute infection. The bacterial burden of bladders infected with either of the representative febrile UPEC isolates was significantly higher than that of bladders infected with either of the non-febrile isolates at 16 hours post inoculation (FIG. 3A). This time point coincides with the maximal influx of PMNs and macrophages into the bladder. Horvath D. J., Jr., et al., Microbes Infect. 13, 426-437 (2011). By 24 hours, bacteria were not recovered from either the bladder or the kidneys of mice infected with the two representative non-febrile isolates (FIG. 3B, C; solid line). The time to clearance of UPEC from both the bladders and the kidneys infected with either of the representative febrile isolates (FIG. 3B, C; dashed line) significantly increased as compared with those tissues infected with either of the representative non-febrile isolates. Therefore, the magnitude of systemic cytokines inversely correlated with persistence in the urinary tract.

Figure 4:
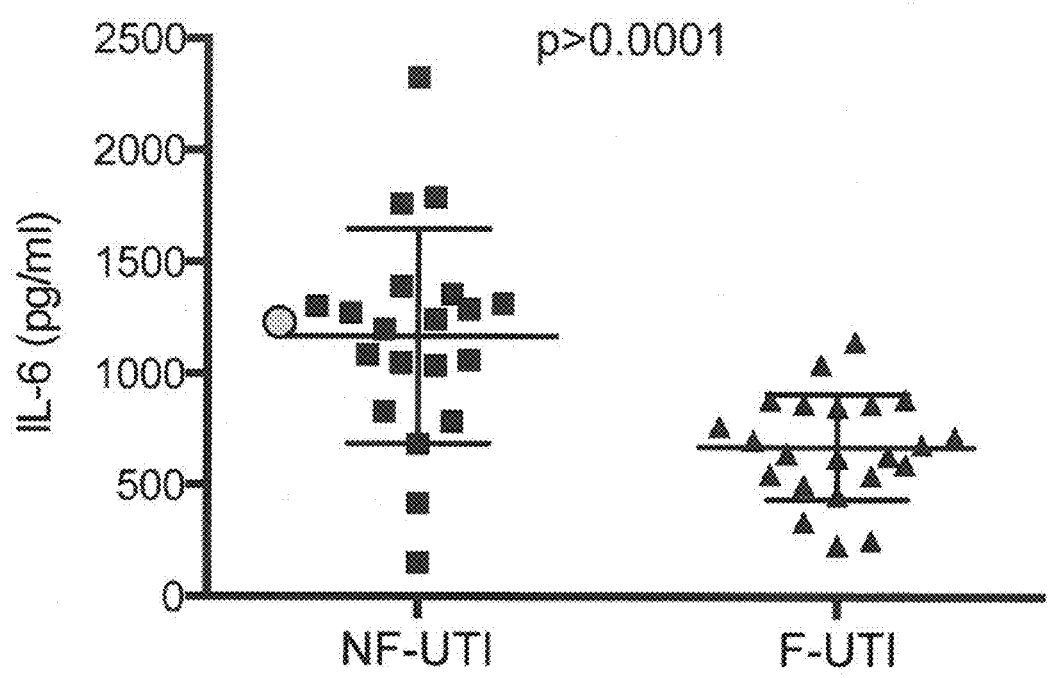
FIG. 4 displays that the magnitude of IL-6 production elicited by conditioned medium is associated with disease presentation. Immortalized human bladder carcinoma cells were stimulated with conditioned medium produced by 35 independent isolates. The IL-6 accumulated in the culture supernatant was quantified by ELISA after 2 hours incubation. Each data point is the average value for the triplicate quantification of each independent isolate. UPEC strains were categorized as non-febrile (NF-UTI; squares) or febrile (F-UTI; triangles) according to the clinical symptoms at the time of isolation from the urine. 95% CI and median values are represented for each group. Statistical significance was determined using a two-tailed Mann Whitney U test.

Magnitude of IL-6 elicitation by conditioned medium is associated with febrile and non-febrile UTI. The concordance of the in vitro and in vivo cytokine profiles provided credence for the use of the in vitro system as an appropriate high throughput first approach for the identification of bacterial factors that modulate the proinflammatory responses. The immunosuppression of cytokine responses by UPEC was abolished when LPS O-antigen synthesis was disrupted. Billips B. K., et al., Infect. Immun. 76, 3891-3900 (2008). In addition, the binding of LPS by the TLR-4 receptor is the predominant signal for proinflammatory responses to bacteria in the urinary tract. Schilling J. D., et al., Infect. Immun. 71, 1470-1480 (2003). (42, 47-49). LPS and other bacterial metabolites accumulate in the culture medium during exponential growth. The clarified culture supernatant is termed "conditioned medium" and has been used previously with mutants defective in assembly of LPS O-antigen. Billips B. K., et al., Infect. Immun. 76, 3891-3900 (2008). Conditioned medium was obtained from each of the 42 isolates within our library to stimulate cultured human bladder epithelial cells in vitro. The inverse correlation of the magnitude of IL-6 pro-inflammatory responses and clinical disease severity observed with the complete panel of viable bacteria was recapitulated with the conditioned media (FIG. 4) (p>0.0001). Storm D. W., et al., J. Urol. 188, 236-241 (2012). Moreover, the magnitude of IL-6 elicitation from all non-febrile isolates was indistinguishable from the conditioned medium of the prototypical and well characterized isolate obtained from a woman with non-febrile cystitis (UTI89, gray circle) (FIG. 4). Therefore, this evidence suggests that one or more constituents of the culture medium contribute to the immunomodulation associated with UPEC isolates.

Figure 5A:
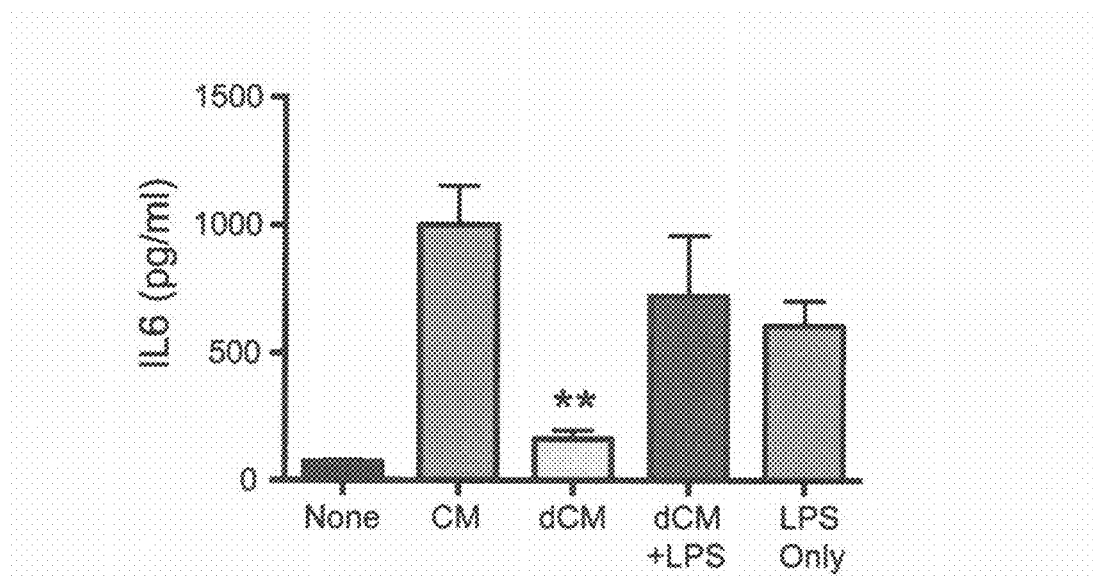
FIGS. 5A and 5B provide graphs showing that depletion of LPS and vesicles from conditioned medium abolishes cytokine elicitation by UTI89. (A) IL-6 elicitation of human bladder epithelial cells was quantified following exposure to conditioned medium (CM), conditioned medium following LPS depletion (dCM), LPS depleted conditioned medium with reconstitution of 1.25 µg/ml commercially available LPS (dCM+LPS), and commercially available LPS alone (LPS only). (B) IL-6 elicitation of UTI89 conditioned medium after removal (−) of vesicles and/or LPS. All samples were normalized using the magnitude detected from parallel non-treated cells. Statistical significance was determined using a two-tailed Mann Whitney U test. (**, $p<0.008$; *, $p=0.03$).
Figure 5B:
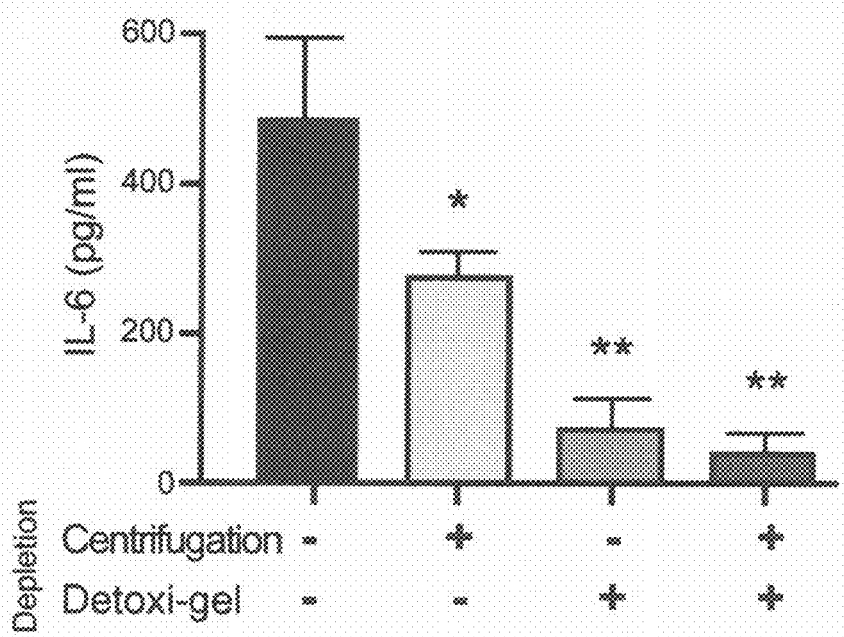

Contribution of LPS to cytokine elicitation in conditioned medium. To begin to define the bacterial factors that contribute to modulation of epithelial proinflammatory responses, we used two approaches to deplete constituents from the conditioned medium. Elicitation of human bladder epithelial cells with conditioned medium from UTI89 was abolished to baseline following a two stage depletion of LPS (p=0.008) (FIG. 4A) with the use of Detoxi-gel Endotoxin resin. Additional passages over the Detoxi-gel Endotoxin Column did not have any additional effect on the magnitude of cytokine elicitation. Reconstitution of the depleted conditioned medium with commercially available LPS resulted in similar levels of IL-6 elicitation as compared to the commercial LPS alone (FIG. 5A), suggesting that the depletion of the LPS abolishes immune stimulation. Bacterial LPS is shed in the form of micelles and outer membrane vesicles. Under these experimental conditions, outer membrane vesicles (and any associated proteins) could have been depleted due to the content of LPS. The magnitude of cytokine elicitation was significantly reduced when outer membrane vesicles were removed by centrifugation (p=0.03) (FIG. 5B). Extraction of residual LPS following removal outer membrane vesicles resulted in IL-6 production that was indistinguishable from uninfected cells (FIG. 5B). Centrifugation of the conditioned medium after LPS depletion did not significantly affect the extent of IL-6 elicitation (FIG. 5B), suggesting that outer membrane vesicles were removed during depletion of the LPS.

Figure 6:
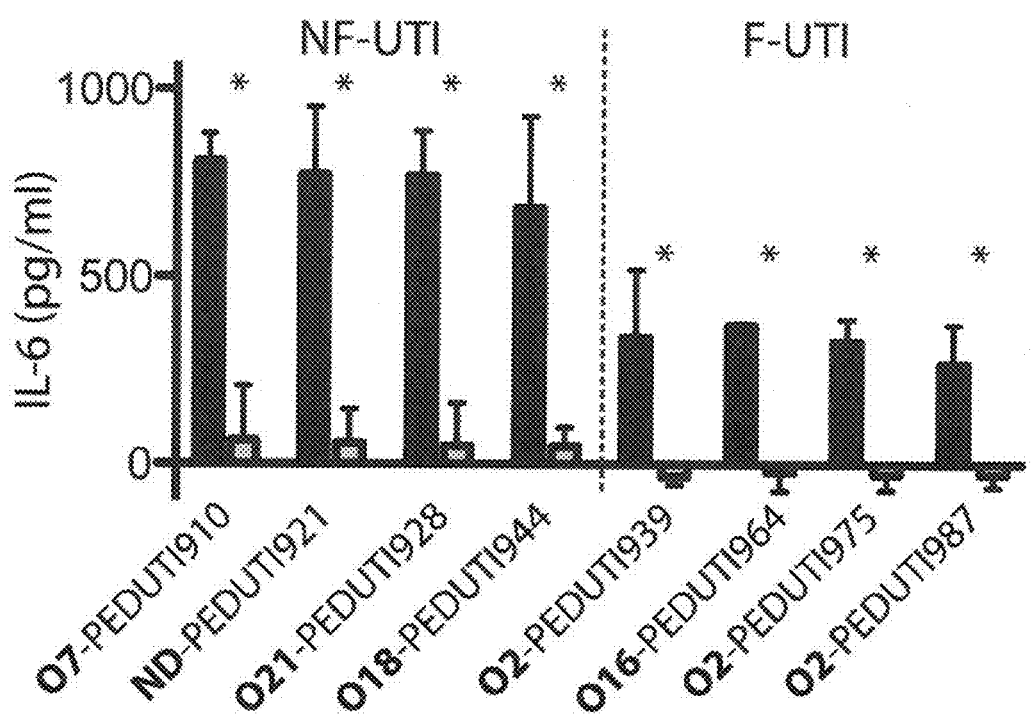
FIG. 6 provides that depletion of LPS abolishes cytokine elicitation of UPEC isolates. Four representative isolates of the non-febrile and febrile isolates evaluated for elicitation of IL-6 in the presence (black bars; +) and absence (gray bars; −) of LPS in the conditioned media are depicted. The serotype and strain name are indicated on the X-axis. Statistical significance was determined using a two-tailed Mann Whitney U test. (*, $p<0.05$)

Since the depletion of LPS by column chromatography was sufficient to remove the elicitation factors from the conditioned medium of UTI89, this methodology was used to evaluate the conditioned medium of all the UPEC isolates. As observed with UTI89, the conditioned medium from the clinical isolates failed to elicit IL-6 production following depletion with the Detoxi-gel resin (four representative febrile and four non-febrile isolates depicted in FIG. 6), suggesting that the molecules that modulate the immune response in the conditioned medium from the clinical isolates are associated with LPS and/or outer membrane vesicles.

Figure 7A:
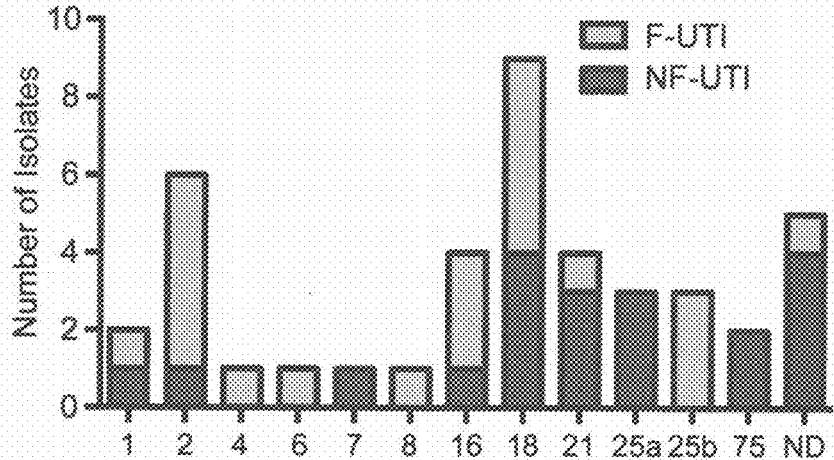
FIGS. 7A and 7B provide graphs showing the association of LPS serotype with clinical disease severity and cytokine responses. (A) Distribution of LPS serotypes from patients that present with non-febrile (dark gray) or febrile (light gray) UTI. The LPS serotype could not be determined (ND) by this method in 5 of the isolates (11%). (B) IL-6 elicitation was determined following infection of cultured bladder epithelial cells with intact viable *E. coli*. Each data point represents the average of three independent replicates. Statistical significance was determined using a one-way ANOVA ($p=0.0001$).

LPS serotype and disease severity. The common bacterial factor depleted from the conditioned medium using both approaches is LPS. Therefore, a potential correlation between the LPS O-antigen serotype and clinical disease severity was evaluated. The LPS serotype was successfully determined for 37 of the 42 UPEC isolates (Table 1). A bias for the presence of certain serotypes with disease presentation was observed (FIG. 7A). Serotypes O2, O16 and O25b were primarily obtained from children with febrile UTI. Conversely, serotypes O21, O25a and O75 were primarily obtained from children with non-febrile infection. The results are consistent with a prior study of 343 UPEC strains that demonstrated an enrichment for serotypes O2 and O16 with pyelonephritis and a lack of association for disease severity with O18. Schilling J. D., et al., Proc. Nat. Acad. Sci. 100, 4203-4208 (2003).

Figure 7B:
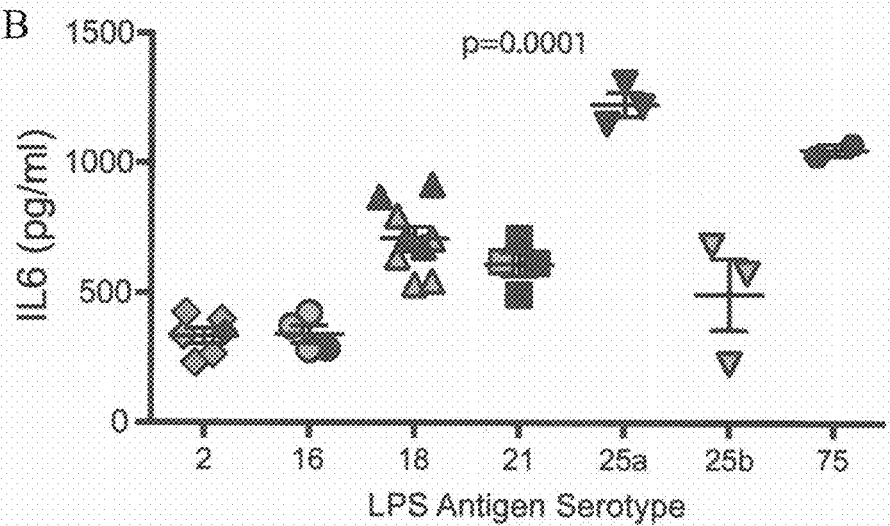
Figure 8:
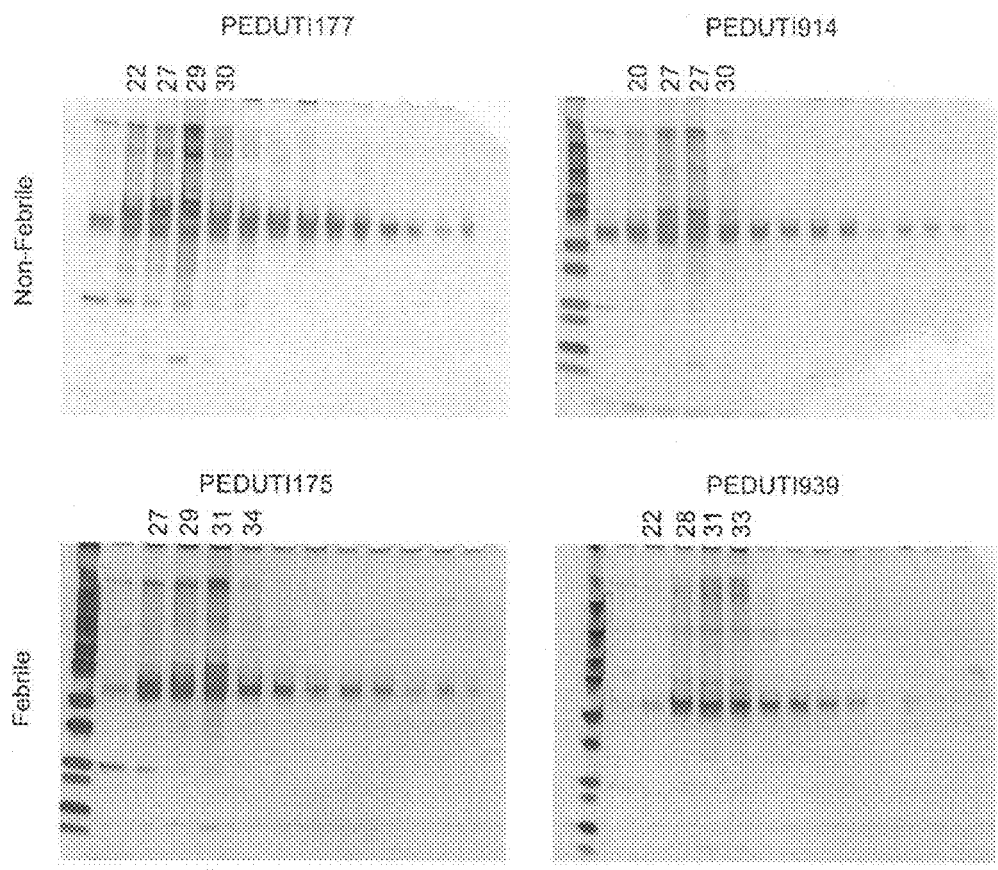
FIG. 8 provides purification of outer membrane vesicles. Each strain indicated 1 was grown in 100 ml of RPMI 1640 containing 10% fetal calf serum at 37° C. overnight until the culture reached saturation. The bacteria were removed by centrifugation and the outer membrane vesicles were isolated from the clarified culture supernatant as previously described. Sharpe S. W., et al., 2011 Infect. Immun. 79, 4361-4369 (2011). In the final step fractions were collected from the OptiPrep-iodixanol (Fisher Scientific) gradient. The protein profiles of each fraction were determined by SDS-PAGE followed by visualization of the protein bands with silver stain. The Optiprep concentration for each fraction containing vesicles was recorded and is indicated on the top of each lane that was pooled for this study. OptiPrep-idixanol was removed from the outer membrane vesicles by centrifugation. Sharpe S. W., et al., 2011 Infect. Immun. 79, 4361-4369 (2011).
Figure 9:
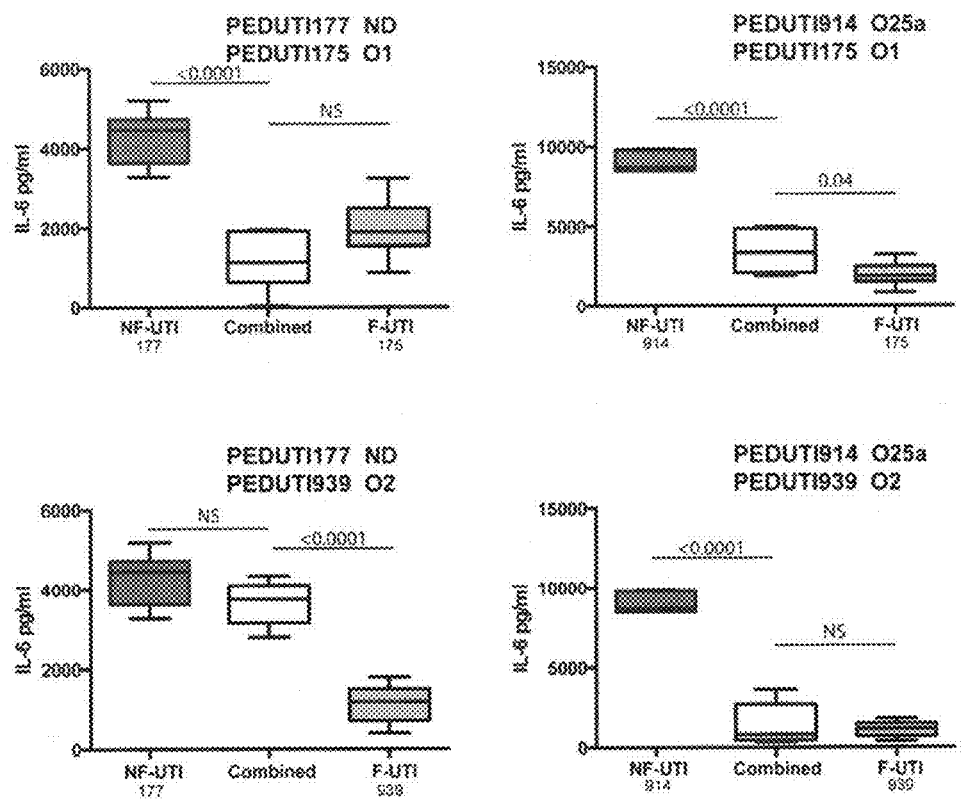
FIG. 9 graphs the elicitation of IL-6 by outer membrane vesicles individually or in combination. The outer membrane vesicles were normalized by protein following quantitation using the Bradford Assay (BioRad, Hercules, Calif.). A total of 5 µg of protein from individual or combined outer membrane vesicles was added to $10^5$ cultured human bladder epithelial cells grown to confluency with three biological replicates. Culture supernatants were collected and clarified after 4 hours of incubation at 37° C. 5% $CO_2$. Secreted IL-6 was quantitated using the Single Analyte ELISArray Kit (SABiosciences, Fredrick, Md.). Statistical significance was determined using an unpaired student t-test (GraphPad Software, La Jolla, Calif.).

LPS serotype and magnitude of cytokine elicitation. To further investigate the association of LPS serotype with the magnitude of cytokine elicitation, IL-6 was quantified from cultured human bladder epithelial cells viable bacteria. Within our collection, certain serotypes were excluded from further evaluation due to statistical limitations (O1, O4, O6, O7, O8) (FIG. 7A). Therefore this analysis included 33 of the isolates from the library. With the exception of serotypes O18 and O25b, the magnitude of cytokines elicited for each independent clinical isolate was very similar within the same serotype (FIG. 7B). The association of the degree of the cytokine elicitation with the LPS serotype of the strain was statistically significant (p=0.0001) (FIG. 7B). Taken together, serotypes O21, O25a and O75 elicit high IL-6 secretion and represent a low risk for progression to febrile infection. In contrast, serotypes O2, O16 and O25b elicit low IL-6 secretion and represent a high risk for progression to a febrile infection. This association was further explored through the evaluation of combinatorial exposure of human bladder epithelial cells to outer membrane vesicles displaying similar protein profiles but exhibiting different LPS serotypes (FIG. 8). Consistent with observations with whole cells (FIG. 7B), we observed differences in the magnitude of IL-6 elicitation when bladder epithelial cells were exposed to outer membrane vesicles from two representative non-febrile isolates (PEDUTI177, PEDUTI914) and two representative febrile isolates (PEDUTI175, PEDUTI 939) (FIG. 9). When the vesicles were mixed, the IL-6 elicitation was representative of one of the two isolates, suggesting that the cells respond to the vesicles produced by only one of the LPS serotypes tested. Therefore, the LPS serotype appears to correlate with the magnitude of IL-6 responses, bacterial persistence, as well as the severity of clinical disease.

Discussion

The specific host-bacterial interactions that transform the disease course leading to enhanced bacterial persistence and disease severity are not completely understood. In our study, we use the same genetic host background (e.g. T24 bladder cells, C3H/HeN mice) to focus only on bacterial attributes that modulate the immune response to elucidate the molecular events that determine disease outcomes. During experimental UTI, the inventors demonstrated that mice infected with UPEC isolates obtained from patients with febrile UTI displayed decreased systemic immune responses and increased bacterial persistence in the urinary tract as compared with mice infected with UPEC isolates obtained from patients with non-febrile UTI. This observation suggests that the rapid clearance of bacteria during experimental UTI is likely a consequence of the high cytokine elicitation that has been observed in vitro. Justice S. S., et al., Infect. Immun. 74, 4793-4800 (2006). Prior studies indicate that bacterial persistence is promoted by two sequential instillations of the prototypical cystitis strain, UTI89, into the bladder 1-6 hours apart. Schwartz D. J., et al., PLoS Pathog. 11, e1004599 (2015). However, increasing the time between the two instillations (>24 hours) nullifies the benefit of superinfection. In light of our data, we suggest that immunosuppression of epithelial responses from the first inoculum could protect the second inoculum from early innate immune responses. The inventors further propose that the enhanced survival of the febrile isolates correlates with a reduction in the recruitment of immune cells combined with a decrease in epithelial production of extracellular and intracellular antibacterial agents. Schwartz D. J., et al., PLoS Pathog. 11, e1004599 (2015). Thus, suppression of the TLR4 cascade provides multiple mechanisms to ensure a more hospitable environment for the expansion of UPEC strains in the urinary tract. The data not only support the use of in vitro systems to investigate epithelial proinflammatory responses to UPEC (Billips B. K., et al., Infect. Immun. 75, 5353-5360 (2007)), but also demonstrate that modulation of the initial inflammatory responses, mediated at the urothelium, has a direct impact on disease progression. As such, these studies provide mechanistic insight into the molecular events that contribute to disease severity.

Bacterial LPS is a very diverse class of molecules. LPS is readily remodeled through modifications of the lipid A moiety (Needham B. D. and Trent M. S., Nat. Rev. Microbiol. 11, 467-481 (2013)), the portion that directly interacts with the TLR4 receptor. Park B. S., et al., Nature 458, 1191-1195 (2009). The ability of lipid A modifications to alter the magnitude of inflammatory responses has been exploited to identify optimal vaccine adjuvants. Needham B. D., et al., Proc. Nat. Acad. Sci. 110, 1464-1469 (2013). Moreover, lipid A mimetics are being investigated as potential therapeutics to enhance or antagonize TLR4 signaling. Lewicky J. D., et al., Bioorg. Med. Chem. 21, 2199-2209 (2013) (57-59). Although each strain appears to only produce one O-antigen, as a species, $E.$ $coli$ can assemble ~158 different sugar moieties onto the lipid A/core complex. Although modifications to the O-antigen within a particular strain participate in pathogenesis (Needham B. D. and Trent M. S., Nat. Rev. Microbiol. 11, 467-481 (2013)), a specific role for the structure of the sugar moiety in pathogenesis is unclear. Given the diversity in LPS O-antigen, the use of isogenic strains is not easily amenable to the direct evaluation of the variations in O-antigen sugar structure during disease. Therefore, the use of a panel of $E.$ $coli$ isolates provided a first line of experimental evidence that the LPS O-antigen moiety is associated with the magnitude of cytokine production. Although the in vitro study focused only on the induction of IL-6, our in vivo evidence suggests that multiple cytokines and chemokines may be modulated by UPEC during UTI. Future studies will include evaluation of an increased repertoire of LPS serotypes to further elucidate the molecular interactions that determine the magnitude of TLR4 responses.

Outer membrane vesicles are produced by a wide variety of bacteria and contribute to pathogenesis and immune modulation. Kim J. H., et al., Semin. Cell Dev. Biol. 40, 97-104 (2015). The inventors observed that outer membrane vesicles retained the ability to modulate the production of IL-6 from cultured bladder epithelial cells. In addition to LPS, proteins and nucleic acids are constituents of outer membrane vesicles. Proteins that are known to regulate proinflammatory responses (e.g. hemolysin, SurA substrates) (Hunstad D. A., et al., Infect. Immun. 73, 3999-4006 (2005)) are packaged into UPEC outer membrane vesicles Wurpel D. J., et al., J. Proteomics 115, 93-106 (2015). Therefore, further biochemical characterization of outer membrane vesicles could identify additional bacterial traits that contribute to the diversity of cytokine responses observed for some LPS serotypes (i.e. O18, 25b).

In summary, the inventors have provided experimental evidence that bacterial persistence correlates with the extent of immunosuppression during the initial stages of infection. Moreover, the LPS serotype, by virtue of the association with magnitude of cytokine elicitation, is associated with the severity of disease.

The complete disclosure of all patents, patent applications, and publications, and electronically available materials cited herein are incorporated by reference. The foregoing detailed description and examples have been given for clarity of understanding only. No unnecessary limitations are to be understood therefrom. In particular, while theories may be presented describing operation of the invention, the inventors are not bound by theories described herein. The invention is not limited to the exact details shown and described, for variations obvious to one skilled in the art will be included within the invention defined by the claims.

What is claimed is:

1. A method of identifying and treating a subject having no underlying anatomical urinary tract infection (UTI) etiology for a urinary tract infection having a significant risk of dangerous sequalae, comprising:
   obtaining a urine or fecal sample from the subject;
   detecting the predominant LPS O-antigen serotype in the sample using an analytic device;
   and treating the UTI of the subject if the predominant O-antigen LPS serotype is a febrile *Escherichia coli* UTI LPS serotype.

2. The method of claim 1, wherein the subject is human.

3. The method of claim 1, wherein the serotype is selected from the group consisting of O2, O16, O21, O25a, O25b, and O75.

4. The method of claim 1, wherein the predominant LPS O-antigen serotype elicits a low IL-6 response.

5. The method of claim 1, wherein one or more of the febrile UTI LPS serotypes are selected from the group consisting of serotypes O2, O16, and O25b.

6. The method of claim 1, wherein the analytic device is a PCR-based assay.

7. The method of claim 1, wherein the subject has been diagnosed as having a urinary tract infection.

8. The method of claim 1, wherein the subject has one or more symptoms associated with a febrile urinary tract infection.

9. The method of claim 1, wherein a subject whose predominant O-antigen LPS serotype is a febrile UTI LPS serotype is treated using an antibiotic.

10. The method of claim 1, wherein a subject whose predominant O-antigen LPS serotype is a febrile UTI LPS serotype is treated by administration of probiotic bacteria.

11. The method of claim 1, wherein the sample is a urine sample.

12. The method of claim 1, wherein the dangerous sequalae are selected from the group consisting of renal scarring, urosepsis, and adverse perinatal outcomes.

* * * * *